United States Patent
Rawas-Qalaji et al.

(10) Patent No.: US 10,682,316 B2
(45) Date of Patent: Jun. 16, 2020

(54) METHODS FOR FABRICATION OF EPINEPHRINE BITARTRATE NANOPARTICLES AND EPINEPHRINE BITARTRATE NANOPARTICLES FABRICATED THEREBY

(71) Applicant: NOVA SOUTHEASTERN UNIVERSITY, Fort Lauderdale, FL (US)

(72) Inventors: Mutasem Rawas-Qalaji, Fort Lauderdale, FL (US); Ousama Rachid, Winnipeg (CA); Keith John Simons, Winnipeg (CA); Estelle Simons, Winnipeg (CA); Enrique Nieves, Fort Lauderdale, FL (US)

(73) Assignee: Nova Southeastern University, Fort Lauderdale, FL (US)

(*) Notice: Subject to any disclaimer, the term of this patent is extended or adjusted under 35 U.S.C. 154(b) by 0 days.

(21) Appl. No.: 15/358,743

(22) Filed: Nov. 22, 2016

(65) Prior Publication Data
US 2017/0071881 A1    Mar. 16, 2017

Related U.S. Application Data

(63) Continuation of application No. 13/582,346, filed as application No. PCT/US2011/026604 on Mar. 1, 2011, now abandoned.

(60) Provisional application No. 61/309,136, filed on Mar. 1, 2010.

(51) Int. Cl.
| A61K 31/137 | (2006.01) |
| A61K 9/19 | (2006.01) |
| A61K 9/00 | (2006.01) |
| A61K 9/14 | (2006.01) |

(52) U.S. Cl.
CPC ............ A61K 31/137 (2013.01); A61K 9/006 (2013.01); A61K 9/14 (2013.01); A61K 9/146 (2013.01); A61K 9/19 (2013.01)

(58) Field of Classification Search
None
See application file for complete search history.

(56) References Cited

U.S. PATENT DOCUMENTS

| 5,143,731 A | 9/1992 | Viegas et al. |
| 5,223,614 A | 6/1993 | Schromm et al. |
| 5,567,439 A | 10/1996 | Myers et al. |
| 5,587,172 A | 12/1996 | Cherukuri et al. |
| 5,622,716 A | 4/1997 | Barth |
| 5,622,717 A | 4/1997 | Fuisz |
| 5,654,003 A | 8/1997 | Fuisz et al. |
| 5,871,781 A | 2/1999 | Myers et al. |
| 6,024,981 A | 2/2000 | Khankari et al. |
| 6,221,392 B1 | 4/2001 | Khankari et al. |
| 6,264,981 B1 | 7/2001 | Zhang et al. |
| 6,309,663 B1 | 10/2001 | Patel et al. |
| 6,368,625 B1 | 4/2002 | Siebert et al. |
| 6,833,377 B2 | 12/2004 | Serdyuk |
| 9,877,921 B2 | 1/2018 | Rawas-Qalaji et al. |
| 10,159,656 B2 | 12/2018 | Rawas-Qalaji et al. |
| 2003/0021841 A1 | 1/2003 | Matharu et al. |
| 2003/0216413 A1 | 11/2003 | Root-Bernstein et al. |
| 2004/0076588 A1 | 4/2004 | Batycky et al. |
| 2004/0234611 A1 | 11/2004 | Ahlheim et al. |
| 2005/0130935 A1 | 6/2005 | Weidner |
| 2006/0093677 A1 | 5/2006 | Chickering et al. |
| 2007/0059361 A1 | 3/2007 | Rawas-Qalaji |
| 2007/0092553 A1 | 4/2007 | Tengler et al. |
| 2007/0122465 A1* | 5/2007 | Desai .................. A61K 9/0019 424/450 |
| 2007/0154549 A1 | 7/2007 | Morton et al. |
| 2007/0202163 A1 | 8/2007 | Rawas-Qalaji et al. |
| 2007/0293580 A1 | 12/2007 | Hill |
| 2008/0032934 A1 | 2/2008 | Behnke et al. |
| 2008/0069779 A1 | 3/2008 | Tamarkin et al. |
| 2009/0263476 A1 | 10/2009 | Jobodevairkkam et al. |
| 2010/0035800 A1 | 2/2010 | Desai et al. |

(Continued)

FOREIGN PATENT DOCUMENTS

| CN | 101669917 | 3/2010 |
| CN | 101669917 A | 3/2010 |

(Continued)

OTHER PUBLICATIONS

Abdelbary et al., "Determination of the In Vitro Disintegration Profile of Rapidly Disintegrating Tablets and Correlation with Oral Disintegration," Int. J. Pharm., 292:29-41(2005).
"Adrenaline into Melanin," Br. Med. J., 2:486 (1971).
Allen, "Rapid-Dissolve Technology: An Interview with Lloyd V. Allen, Jr. PhD, RPh," Int. J. Pharm. Compound., 7:449-450 (2003).
Aly et al., "Superdisintegants for Solid Dispersion to Produce Rapidly Disintegrating Tenoxicam Tablets via Camphor Sublimation," Pharm. Tech., 7:68-78 (2005).
Aurora et al., "Oral Disintegrating Dosage Forms: An Overview," Drug Deliv. Technol., 5:50-54 (2005).

(Continued)

Primary Examiner — Bethany P Barham
Assistant Examiner — Dominic Lazaro
(74) Attorney, Agent, or Firm — Fleit Intellectual Property Law; Paul D. Bianco; Katharine Davis Wong

(57) ABSTRACT

The invention provides a composition including epinephrine nanoparticles and methods for therapeutic use of the composition in the treatment of conditions responsive to epinephrine such as a cardiac event or an allergic reaction, particularly anaphylaxis. The epinephrine nanoparticles can be incorporated into orally-disintegrating and fast-disintegrating tablet pharmaceutical formulations and can significantly increase the sublingual bioavailability of epinephrine, and thereby reduce the epinephrine dose required. Additionally, the invention provides methods for fabrication of stabilized epinephrine nanoparticles for use in the described compositions.

6 Claims, 6 Drawing Sheets

(56) References Cited

U.S. PATENT DOCUMENTS

| | | |
|---|---|---|
| 2011/0182005 A1 | 7/2011 | Yuan |
| 2011/0182805 A1 | 7/2011 | DeSimone et al. |
| 2011/0223203 A1 | 9/2011 | Berkland et al. |
| 2011/0250278 A1 | 10/2011 | Yuan |
| 2012/0322884 A1 | 12/2012 | Rawas-Qalaji et al. |
| 2014/0242177 A1 | 8/2014 | Rawas-Qalaji et al. |
| 2014/0364513 A1 | 12/2014 | Park et al. |
| 2015/0164827 A1 | 6/2015 | Rawas-Qalaji et al. |
| 2016/0045457 A1 | 2/2016 | Rawas-Qalaji |
| 2016/0374966 A1 | 12/2016 | Rawas-Qalaji et al. |
| 2017/0000735 A1 | 1/2017 | Rawas-Qalaji et al. |
| 2017/0020827 A1 | 1/2017 | Rawas-Qalaji |
| 2017/0071881 A1 | 3/2017 | Rawas-Qalaji et al. |
| 2018/0147145 A1 | 5/2018 | Rawas-Qalaji et al. |
| 2019/0125698 A1 | 5/2019 | Rawas-Qalaji |
| 2019/0231716 A1 | 8/2019 | Rawas-Qalaji |

FOREIGN PATENT DOCUMENTS

| | | | |
|---|---|---|---|
| EP | 0159237 | 10/1985 | |
| EP | 0159237 A1 | 10/1985 | |
| EP | 2753321 A1 | 7/2014 | |
| WO | 1994/09762 | 11/1993 | |
| WO | WO 1994/009762 A1 | 5/1994 | |
| WO | 2005/63203 | 12/2004 | |
| WO | 2007/028247 | 3/2007 | |
| WO | 2007/143674 A2 | 12/2007 | |
| WO | 2007143674 A2 | 12/2007 | |
| WO | 2008058755 A1 | 5/2008 | |
| WO | WO-2008058755 A1 * | 5/2008 | ............. A61K 8/044 |
| WO | 2008-095284 | 8/2008 | |
| WO | 2011/109340 | 9/2011 | |
| WO | 2011109340 A1 | 9/2011 | |
| WO | 2013-059629 | 4/2013 | |
| WO | 2013/059629 | 4/2013 | |
| WO | 2013059629 | 4/2013 | |
| WO | 2014/007972 | 1/2014 | |
| WO | 2014/153559 | 9/2014 | |
| WO | WO 2014/153559 A1 | 9/2014 | |

OTHER PUBLICATIONS

BI et al., "Evaluation of Rapidly Disintegrating Tablets Prepared by a Direct Compression Method," Drug Dev. Ind. Pharm., 25:571-581 (1999).

BI et al., "Preparation and Evaluation of a Compressed Tablet Rapid Disintegration in the Oral Cavity," Chem. Pharm. Bull., 44:2121-2127 (1996).

Birudaraj et al., "Buccal Permeation of Bispirone: Mechanistic Studies on Transport Pathways," J. Pharm. Sci., 94:70-78 (2004).

Chang et al., "Fast Dissolving Tablets," Pharm. Tech., 24:52-58 (2000).

Connors et al., "Epinephrine," in Chemical Stability of Pharmaceuticals: A Handbook for Pharmacists, Wiley-Interscience Publication: New York, 1986, pp. 438-447.

Cunningham et al., "Comparative Pharmacokinetics of Oral Versus Sublingual Clonidine," J. Clin. Anesth., 6:430-433 (1994).

De Vries et al., "Developments in Buccal Drug Delivery," Crit. Rev. Ther. Drug Can. Syst., 8:271-303 (1991).

Dobetti, "Fast-Melting Tablets: Developments and Technologies," PharmTech. Eur., 12:32-42 (2000).

Dor et al., "In Vitro Determination of Disintegration Time of Quick-Dissolve Tablets Using a New Method," Pharm. Dev. Technol., 5:575-577 (2000).

El-Arini et al., "Evaluation of Disintegration Testing of Different Fast Dissolving Tablets Using the Texture Analyser," Pharm. Dev. Technol., 7:361-371 (2002).

Fell et al., "Determination of Tablet Strength by the Diametral Compression Test," J. Pharm. Sci., 59:688-691 (1970).

Ganhao et al., "Evaluation of a Single Plasma Catecholamino Extraction Procedure Prior to High-Performance Liquid Chromatography and Electrochemical Detection," J. Chromatogr., 564:55-66 (1991).

Gu et al., "Is Epinephrine Administration by Sublingual Tablet Feasible for the First-Aid Treatment of Anaphylaxis? A Proof of Concept Study," Biopharm. Drug Dispos., 23:213-216 (2002).

Gu et al., "Epinephrine Absorption After Different Routes of Administration in an Animal Model," Biopharm. Drug Dispos., 20:401-405 (1999).

Hamilton et al., "Advanced Orally Disintegrating Tablets Bring Significant Benefits to Patients and Product Life Cycles," Drug Deliv. Technol., 5:34-37 (2005).

Hedenus et al., "Characterization of Instantaneous Water Absorption Properties of Pharmaceutical Excipients," Int. J. Pharm., 141:141-149 (2000).

Hjemdahl, "Catecholamine Measurements in Plasma by High-Performance Liquid Chromatography With Electrochemical Detection," Methods Enzymol., 142:521-534 (1987).

Hjemdahl, "Inter-Laboratory Comparison of Plasma Catecholamine Determinations Using Several Different Assays," Acta Physiol. Scand. Suppl., 527:43-54 (1984).

"Human Physiology: From Cells to Systems," Sherwood ed.; Brooks/Cole/Thomson Learning: Belmont, CA, 2004; Chapter 16, pp. 591-645.

Ishikawa et al., "Pharmacokinetics of Acetaminophen From Rapidly Disintegrating Compressed Tablet Prepared Using Microcrystalline Cellulose (PH-M-06) and Spherical Sugar Granules," Chem. Pharm. Bull., 49:230-232 (2001).

Ishikawa et al., "Preparation of Rapidly Disintegrating Tablet Using New Types of Microcrystalline Cellulose (PH-M Series) and Low Substituted-Hydroxypropylcellulose or Spherical Sugar Granule by Direct Compression Method," Chem. Pharm. Bull., 49:134-139 (2001).

Kroboth et al., "Triazopam Pharmalinetics After Intravenous, Oral, and Sublingual Administration," J. Clin. Psychopharmacol., 15:259-262 (1995).

Lieberman et al., "Joint Task Force on Practice Parameters," J. Allergy Clin. Immunol., 115:S483-S523 (2005).

Lieberman et al., "Use of Epinephrine in the Treatment of Anaphylaxis," Curr. Opin. Allergy Clin. Immunol., 3:313-318 (2003).

Mitra et al., "Peptides and Proteins—Buccal Absorption," Encyclopedia of Pharm. Tech., pp. 2081-2095 (2002).

Motwani and Lipworth, "Clinical Pharmacokinetics of Drugs Administered Buccaly and Sublingually," Clin. Pharmacokinet., 21:83-94 (1991).

Parakh et al., "A Review of Mouth Dissolving Tablet Technologies," Pharm. Tech. 27:92-100 (2003).

Physical Tests: Dissolution (711); 22/17 ed., Rockville, MD: United States Pharmaceutical Convention Inc., 2007.

Price et al., "Single-Dose Pharmacokinetics of Sublingual Versus Oral Administration of Micronized 17β-Estradiol," Obstet. Gynecol., 89:340-345 (1997).

Rachid et al., "An Electronic Tongue: Evaluation of the Masking Efficacy of Sweetening and/or Flavoring Agents on the Bitter Taste of Epinephrine," AAPS PharmSciTech, 11:550-557 (2010).

Rachid et al., "Dissolution Testing of Sublingual Tablets: a Novel In Vitro Method," AAPS PharmSciTech, 12:544-552 (2011).

Rawas-Qalaji et al., "Fast-Disintegrating Sublingual Epinephrine Tablets: Effect of Drug and Tablet Dimensions on Tablet Characteristics," AAPS 7(52): Abstract W5220 (2005).

Rawas-Qalaji et al., "Sublingual Epinephrine Tablets Versus Intramuscular Injection of Epinephrine: Dose Equivalence for Potential Treatment of Anaphylaxis," J. Allergy Clin. Immunol, 117:398-403 (2006).

Rawas-Qalaji et al., "Fast-Disintegrating Sublingual Epinephrine Tablets: Effect of Epinephrine Load on Tablet Characteristics," AAPS PharmSciTech, 7:E1-E7 (2006).

Rawas-Qalaji et al., "Fast-Disintegrating Sublingual Epinephrine Tablets: Long Term Stability Study," AAPS 7(52) Abstract W5219 (2005).

Rawas-Qalaji et al., "Formulation of Fast-Disintegrating Sublingual Epinephrine Tablets for the First-Aid Treatment of Anaphylaxis Away from Health Care Facilities," AAPS 6(4) Abstract W4178 (2004).

Rawas-Qalaji et al., "Evaluation of the Effect of Changing Tablet Dimensions on the Characteristics of Fast-Disintegrating Sublingual

(56) References Cited

OTHER PUBLICATIONS

Epinephrine Tablets for the First-Aid Treatment of Anaphylaxis Away from Health Care Facilities," AAPS 6(4) Abstract W4179 (2004).
Rawas-Qalaji et al., "Epinephrine for the Treatment of Anaphylaxis: Do All 40 mg Sublingual Epinephrine Tablet Formulations with Similar In Vitro Characteristics Have the Same Bioavailability?" Biopharm. Drug Dispos., 27:427-435 (2006).
Rawas-Qalaji et al., "Development of Epinephrine Nanoparticles Using Chitosan for the Treatment of Anaphylaxis," Poster Presentation at the 2011 AAPS Annual Meeting and Exposition, Oct. 23-27, 2011, Washington DC, Poster No. W4174.
Sastry et al., "Drug Delivery to the Oral Cavity: Molecule to Market," Chapter 13, pp. 311-316 (2005), Taylor & Francis, CRC Press.
Sastry et al., "Recent Technological Advances in Oral Drug Delivery—A Review," Pharm. Sci. Technol. Today, 3:138-145 (2000).
Saxena, "Sublingual Versus Vaginal Route of Misoprostol for Cervical Ripening Prior to Surgical Termination of First Trimester Abortions," Eur. J. Odst. Gynecol. Reprod. Biol., 125:19-113, (2006).
Scavone et al., "The Pharmacokinetics and Pharmacodynamics of Sublingual and Oral Alprazolam in the Post-Prandial State," Eur. J. Clin. Pharmacol., 42:439-443 (1992).
Schiermeier et al., "Fast Disposable Ibuprophen Tablets," Eur. J. Pharm. Sci., 15:295-305 (2002).
Sharma et al., "Manufacturing Technology Choices for Mouth Dissolving Tablets," Pharm. Tech. North America, 10-15 (2003).
Sigma-Aldrich, Material Safety Data Sheet, Version 3.2, printed May 1, 2012.
Simons, "First-Aid Treatment of Anaphylaxis to Food: Focus on Epinephrine," J. Allergy Clin. Immunol., 113:837-844 (2004).
Simons et al., "Sublingual Epinephrine Administration in Humans: A Preliminary Study," J. Allergy Clin. Immunol , 113:S260 (2004).
Simons, "EpiPen Jr Versus EpiPen in Young Children Weighing 15 to 30 kg at Risk for Anaphylaxis," J. Allergy Clin. Immunol , 109:171-175 (2002).
Simons, "Outdated EpiPen and EpiPen Jr Autoinjections: Past Their Prime?" J. Allergy Clin. Immunol., 105:1025-1030 (2000).
Simons, "Anaphylaxis: Recent Advances in Assessment and Treatment," J. Allergy Clin. Immunol., 124(4):625-636 (2009).
Simons, "Anaphylaxis," J. Allergy Clin. Immunol., 125:S161-S181 (2010).
Simons, et al., "Epinephrine and Its Use in Anaphylaxis", Curr. Opin. Clin. Immunol., 10:354-361 (2010).
Spenard et al., "Placebo-Controlled Comparative Study of the Anxiolytic Activity and of the Pharmacokinetics of Oral and Sublingual Lorazepam in Generalized Anxiety," Biopharm. Drug Dispos., 9:457-464 (1988).
Sugimoto et al., "The Preparation of Rapidly Disintegrating Tablets in the Mouth," Pharm. Dev. Technol., 6:487-493 (2001).
Verm et al., "Current Status of Drug Delivery Technologies and Future Directions," Pharm. Technol., 25:1-4 (2001).
Watenabe et al., "New Compressed Tablet Rapidly Disintegrating in Saliva in the Mouth Using Crystalline Cellulose and a Disintegrant," Biol. Pharm. Bull., 18:1308-1310 (1995).
International Preliminary Report and Written Opinion dated May 1, 2014 for PCT/US2013/045836.
Kemp SF, Lockey RF, Simons FE Epinephrine: the drug of choice for anaphylaxis. A statement of the World Allergy Organization. Allergy 2008; 63:1061-70.
McLean-Tooke AP, Bethune CA, Fay AC, Spickett GP. Adrenaline in the treatment of anaphylaxis: what is the evidence? BMJ 2003; 327:1332-5.
Simons KJ, Simons FE. Epinephrine and its use in anaphylaxis: current issues. Curr Opin Allergy Clin Immunol 2010; 10:354-61.
Soar J, Pumphrey R, Cant A, Clarke S, Corbett A, Dawson P, et al. Emergency treatment of anaphylactic reactions—guidelines for healthcare providers. Resuscitation 2008; 77:157-69.

Simons FE Epinephrine auto-injectors: first-aid treatment still out of reach for many at risk of anaphylaxis in the commmunity. Ann Allergy Asthma Immunol 2009; 102:403-9.
Simons FER. Lack of worldwide availability of epinephrine autoinjectors for outpatients at risk of anaphylaxis. Ann Allergy Asthma Immunol 2005; 94:534-8.
Bredenberg S, Duberg M, Lennernas B, Lennernas H, Pettersson A, Westerberg M et al. In vitro and in vivo evaluation of a new sublingual tablet system for rapid oromucosal absorption using fentanyl citrate as active substance. Eur J Pharm Sci 2003; 20:327-34.
Glover ED, Glover PN, Franzon M, Sullivan CR, Cerullo CC, Howell RM, et al. A comparison of a nicotine sublingual tablet and placebo for smoking cessation. Nicotine Tob Res 2002; 4:441-50.
Guez S. Efficacy of desensitization via the sublingual route in mite allergy. Chem Immunol Allergy 2003; 82:62-76.
Rawas-Qalaji MM, Simons FE, Simons KJ. Sublingual epinephrine tablets versus intramuscular injection of epinephrine: Dose equivalence for potential treatment of anaphylaxis. J Allergy Clin Immunol 2006; 117:398-403.
Rawas-Qalaji MM, Simons FE, Simons KJ. Epinephrine for the treatment of anaphylaxis: do all 40 mg sublingual epinephrine tablet formulations with similar in vitro characteristics have the same bioavailability? Biopharm Drug Dispos 2006; 27:427-35.
Saxena P, Salhan S, Sarda N. Sublingual versus vaginal route of misoprostol for cervical 20 ripening prior to surgical termination of first trimester abortions. Eur J Obstet Gynecol Reprod Biol, 125:109-113, 2006.
Chapter 8, Neurotransmission: The Autonomic and Somatic Motor Nervous Systems In Goodman & Gilman's The Pharmacological Basis of Therapeutics. 12 ed., 16 pages, 2011.
Rachid O, Simons FE, Rawas-Qalaji M, Simons KJ. An electronic tongue: evaluation of the masking efficacy of sweetening and/or flavoring agents on the bitter taste of epinephrine. AAPS PharmSciTech 2010; 11:550-7.
Rawas-Qalaji MM, Simons FE, Simons KJ. Fast-disintegrating sublingual epinephrine 30 tablets: effect of tablet dimensions on tablet characteristics. Drug Dev Ind Pharm 2007; 33:523-30.
Rawas-Qalaji MM, Simons FER, Simons KJ. Fast-Disintegrating Sublingual Tablets: Effect of Epinephrine Load on Tablet Characteristics. AAPS PharmSciTech 2006; 7: Article 41.
Muller RH, Gohla S, Keck CM. State of the art of nanocrystals â€ Special features, production, nanotoxicology aspects and intracellular delivery. European Journal of Pharmaceutics and Biopharmaceutics; 78:1-9.
USP/NF. Physical Tests: Uniformity of Dosage Units (905). 31/26 ed. Rockville, MD: United States Pharmacopeial Convention, Inc.; 2008.
USP/NF. Official Monograph: Epinephrine Injection. 31/26 ed. Rockville, MD: United States Pharmacopeial Convention, Inc.; 2008.
USP/NF. Physical Tests: Tablet Friability (1216). 31/26 ed. Rockville, MD: United States Pharmacopeial Convention, Inc.; 2008.
Olfert ED, Cross BM, McWilliam AA. Guide to the care and use of experimental animals. 2 ed. Ottawa: Canadian Council on Animal Care; 1993.
Hjemdahl P. Inter-laboratory comparison of plasma catecholamine determinations using several different assays. Acta Physiol Scand Suppl 1984; 527:43-54.
Hjemdahl P. Catecholamine measurements in plasma by high-performance liquid chromatography with electrochemical detection. Methods Enzymol 1987; 142:521-34.
Ganhao MF, Hattingh J, Hurwitz ML, Pills NI. Evaluation of a simple plasma catecholamine extraction procedure prior to high-performance liquid chromatography and electrochemical detection. J Chromatogr 1991; 564:55-66.
Rachid O, Rawas-Qalaji M, Simons FE, Simons KJ. Rapidly-disintegrating sublingual tablets of epinephrine: role of non-medicinal ingredients in formulation development. Eur J Pharm Biopharm 2012; 82:598-604.

(56) References Cited

OTHER PUBLICATIONS

Rachid O, Rawas-Qalaji MM, Simons FE, Simons KJ. Epinephrine (adrenaline) absorption from new-generation, taste-masked sublingual tablets: a preclinical study. J Allergy Clin Immunol 2013; 131:236-8.
Liu Y, Sun C, Hao Y, Jiang T, Zheng L, Wang S. Mechanism of dissolution enhancement and bioavailability of poorly water soluble celecoxib by preparing stable amorphous nanoparticles. J Pharm Pharm Sci 2010; 13:589-606.
Ma Q, Sun H, Che E, Zheng X, Jiang T, Sun C, et al. Uniform nano-sized valsartan for dissolution and bioavailability enhancement: Influence of particle size and crystalline state. Int J Pharm 2013; 441:75-81.
Dali MM, Moench PA, Mathias NR, Stetsko PI, Heran CL, Smith RL. A rabbit model for sublingual drug delivery: comparison with human pharmacokinetic studies of propranolol, verapamil and captopril. J Pharm Sci 2006; 95:37-44.
Ong CM, Heard CM. Permeation of quinine across sublingual mucosa, in vitro. Int J Pharm 2009; 366:58-64.
International Search Report dated Jan. 16, 2014 for PCT/US2013/045836.
Written opinion dated Jan. 16, 2014 for PCT/US2013/045836.
Rawan-Qalaji et all, Development of Epinephrine Nanoparticles Using Chitosan for the Treatment of Anaphylaxis, Poster presentation at the 2011 AAPS Annual Meeting and Exposition, Oct. 23-27, 2011, Washington DC, Poster No. W4174.
Adrenaline into Melanin, Br Med J, May 29, 2971, 2(5760): 486.
Saxena, Sublingual versus vaginal route of misoprostol for cervical ripening prior to surgical termination of first timrester abortions, Eur J Obstet Gynecol Reprod Biol Mar. 1, 2006, 125(1): 109-13, abstract.
International Search Report dated Aug. 20, 2014, Written Opinion dated Aug. 20, 2014 and International Preliminary Examination Report dated Sep. 22, 2015 for PCT/US14/31579.
Birudaraj et al., 2004, J Pharm Sci 94.
Ishikawa et al., 2001, Chem Pharm Bull 49: 230-23.
Price et al., 1997, Obstet Gynecol 89: 340-345.
Kroboth et al., 1995, J Clin Psychopharmacol 15: 259-262.
Cunningham et al., 1994, J Clin Anesth 6: 430-433.
Scavone et al., 1992, Eur J Clin Pharmacol 42: 439-443.
Spenard et al., 1988, Biopharm Drug Dispos 9: 457-464.
Mitra et al., 2002, Encyclopedia of Pharm. Tech., 2081-2095.
Joint Task Force on Practice Parameters, 2005, J Allergy Clin Immunol 115: S483-S523.
Lieberman, 2003, Curr Opin Allergy Clin Immunol 3: 313-318.
Simons, 2004, J Allergy Clin Immunol 113: 837-844, First-Aid Treatment of Anaphylaxis to Food, 8 pgs.
Simons, F.E.R. J Allergy Clin Immunol 124(4):625-636 2009, Anaphylaxis: Recent Advances in Assessment and Treatment, 12 pgs.
Simons, F.E.R. J Allergy Clin Immunol 125:S161-181 2010, Anaphylaxis, 21 pgs.
Simons, K.J. et al. Current Opinion in Clinical Immunology 10:354-361 2010, Epinephrine and Its use in Anaphylaxis, 8 pgs.
Connors et al., 1986, in Chemical Stability of Pharmaceuticals: A Handbook for Pharmacists, Wiley-Interscience Publication: New York.
Gu et al., 2002, Biopharm Drug Dispos 23: 213-216.
Simons et al., 2004, J Allergy Clin Immunol 113: 425-438, S260 Abstract.
Rawas-Qalaji et al. J Allergy Clin Immunol 117:398-403 2006.
Rawas-Qalaji et al. Biopharm Drug Disposition 27 (9):427-435 2006.
AAPS PharmSciTech 12:544-552,2011.
Rachid, O. et al. AAPS PharmSciTech 12(2):544-552 2011.
USP/NF. Physical Tests: Dissolution (711); 22/17 ed. Rockville, MD: United States Pharmaceutical Convention Inc; 2007.
Rachid, O. et al. AAPS PharmSciTech 11(2):550-557 2010.
Rawas-Qalaji, AAPS PharmSciTech. 2006;7(2): Article 41.
Motwani et al., 1991, Clin Pharmacokinet 21: 83-94.

Written Opinion dated Apr. 29, 2011 for PCT/US11/26604 filed Mar. 1, 2010.
International Search Report dated Apr. 29, 2011 for PCT/US11/26604 filed Mar. 1, 2010.
Written Opinion dated Jan. 11, 2013 for PCT/US12/061074 filed Oct. 19, 2012.
International Search Report dated Jan. 11, 2013 for PCT/US12/061074 filed Oct. 19, 2012.
European Search Report for EP12842206 dated Mar. 31, 2015, 7 pages (national stage of PCT/US2012/61074 published as WO2013/59629).
Ting Qiao et al, Conjugation of catecholamines on magnetic nanoparticles coated with sulfonated chitosan, Colloids and Sufaces A: Physicochem, Eng. Aspects 380 (2011) 169-174.
Simons, Is epinephrine administration by sublingual table feasible for the first-aid treatment of anaphylaxes?, Biopharm Drup Dispos, 2002, Jul. 23 (5): 213-6, abstract.
International Preliminary Report on Patentability and Written Opinion for PCT/US13/45836 filed Jun. 14, 2013.
PubcheM: title: chemical and physical properties of epinephrine (only pertinent pages of 1 and 8), downloaded on Jun. 6, 2016, from http:/dav.uspto.gove/webappapplicationViewer.html?casenumber_14778887#).
Spyros Papiris, et al, Clinical Review: Severe Asthma, Critical Care. vol. 6(1), p. 30-44, published online Nov. 22, 2001.
International Search Report dated Dec. 22, 2006, Written Opinion dated Dec. 22, 2006 and International Prelim Report on Patentability dated Dec. 10, 2007, for PCT/CA06/001472.
International Search Report dated Apr. 29, 2008, Written Opinion dated Apr. 29, 2008 and International Prelim Report on Patentability dated Apr. 11, 2009, for PCT/CA08/00197.
Office action dated Mar. 16, 2009 for U.S. Appl. No. 11/672,503.
Written Opinion dated Jan. 11, 2013 and International Prelim Report on Patentability dated Apr. 22, 2014, for PCT/US2012/061074.
International Search Report dated Jan. 11, 2013 for PCT/US2012/061074.
International Prelim Report on Patentability dated Sep. 4, 2012 for PCT/US2011/26604.
Office action dated Mar. 13, 2009 for U.S. Appl. No. 11/530,360.
For U.S. Appl. No. 13/582,346 office actions dated Sep. 12, 2013; Feb. 7, 2014 response dated Dec. 12, 2013.
Office Action dated Nov. 17, 2015 for EP 14768584 (national stage of PCT/US2014/31579).
Abdelbary, G. et al., "Determination of the in vitro disintegration profile of rapidly disintegrating tablets and correlation with oral disintegration," Int. J. Pharm. 292:29-41 (2005).
Allen, L., "Rapid-Dissolve Technology: An Interview with Lloyd V. Allen, Jr. PhD, RPh," Int. J. of Pharma. Compounding 7:449-450 (2003).
Aly, A, et al., "Superdisintegrantsfor Solid Dispersion to Produce Rapidly Disintegrating TenoxicamTablets via Camphor Sublimation," Pharma. Tcch.7:68-78 (2005).
Aurora, I. And Pathak, V., "Oral Disintegrating Dosage Forms: An Overview," Drug Deliv. Technol. 5:50-54 (2005).
BI, Y.X. et al., Evaluation of Rapidly Disintegrating Tablets Prepared by a Direct Compression Method, Drug Dev. Ind. Pharm. 25:571-581 (1999).
BI, Y. et al., "Preparation and Evaluation of a Compressed Tablet Rapidly Disintegrating in the Oral Cavity," Chem. Pharm. Bull. 44:2121-2127 (1996).
Birudaraj, R. et al., "Buccal Permeation of Buspirone: Mechanistic Studies on Transport Pathways," J. Pharm. Sci. 94:70-78 (2004).
Chang, R. et al., "Fast-Dissolving Tablets," Pharm. Tech. 24:52-58 (2000).
Cunningham, F. et al, "Comparative Pharmacokinetics of Oral versus Sublingual Clonidine," J. Clin, Anesth, 6:430-433 (1994).
De Vries, M, et al., "Developments in Buccal Drug Delivery," Crit, Rev. Ther. Drug Carr. Syst. 8:271-303 (1991).
Dobetti, L., "Fast-Melting Tablets: Developments and Technologies," Pharmaceutical Technology Europe 12:32-42 (2000).
Dor, P. And Fix, J., "In Vitro Determination of DisintegrationTime of Quick-Dissolve Tablets Using a New Method," Pharm. Dev. Technol. 5:575-577 (2000).

(56) References Cited

OTHER PUBLICATIONS

BL-Arini, S. and Clas, S., "Evaluation of Disintegration Testing of Different Fast Dissolving Tablets Using the Texture Analyzer," Pharm. Dev. Technol. 7:361-371 (2002).

Fell,. J.T. and Newton, J.M., "Determination of Tablet Strength by the Diametral-Compression Test," J. Pharm. Sci. 59:688-691 (1970).

Ganhao, M. et al, "Evaluation of a simple plasma catecholamino extraction procedure prior to high-performance liquid chromatography and electrochemical detection," J. Chromatogr, 564;55-66 (1991).

Gu, X. et al., "Is Epinephrine Administration by Sublingual Tablet Feasible for the First-Aid Treatment of Anaphylaxis? A Proof-Of-Concept Study," Biopharm. Drug. Dispos. 23:213-216 (2002).

Gu, X., et al., "Epinephrine Absorption alter Different Routes of Administration in an Animal Model," Biopharm Drug Dispos, 20: 401-405 (1999).

Hamilton, E. et al., "Advanced Orally Disintegrating Tablets Bring Significant Benefits to Patients & Product Life Cycles," Drug Deliv. Technol. 5:34-37 (2005).

Hedenus, P. et al., "Characterisation of instantaneous water absorption properties of pharmaceutical excipients," Int. J. Pharm. 141:141-149 (2000).

Hjemdahl, P., "Catecholamine Measurements in Plasma by High-Performance Liquid Chromatography with Electrochemical Detection," Methods in Enzymol. 142:521-534 (1987).

Hjemdahl, P., "Inter-laboratory comparison of plasma catecholamine determinations using several different assays," Acta Physiol. Scand. Suppl. 527:43-54 (1984).

*Human Physiology: From Cells to Systems*, Sherwood L., (ed.) Brooks/Cole/Thomson Learning: Belmont, CA, 2004; Chapter 16, pp. 591-645.

Ishikawa, T. et al., "Pharmacokinetics of Acatominophen from Rapidly Disintegrating Compressed Tablet Prepared Using Microcrystalline Collulose (PH-M-06) and Spherical Sugar Granules," Chem Pharm. Bull. 48:230-232 (2001).

Ishikawa, T. et al., "Preparation of Rapidly Disintegrating Tablet Using New Types of Microcrystalline Cellulose (PH-M Series) and Low Substituted-Hydroxypropylcellulose or Spherical Sugar Granules by Direct Compression Mehod," Chem. Pharm. Bull. 49:134-139 (2001).

Kroboth, P. et al., "Triazopam Pharmacolcinetics After Intravenous, Oral, and Sublingual Administration," J. Clin. Psychopharmacol. 15:259-262 (1995).

Lieberman, P. et al., "Joint Task Force on Practice Parameters," J. Allergy Clin. Immunol. 115:S483-S523 (2005).

Lieberman, P., "Use of epinephrine in the treatment of anaphylaxis," Curr. Opin. Allergy Clin. Immunol, 3:313-318 (2003).

Mitra, A. et al., "Peptides and Proteins—Buccal Absorption," Encyclopedia of Pharm. Tech., pp. 2081-2095 (2002).

Motwani, J. and Lipworth, B., "Clinical Pharmacokinetics of Drugs Administered Buccally and Sublingually," Clin. Pharmacokinet. 21:83-94 (1991).

Parakh, S.R. And Gothoskar, A.V., "A Review of Mouth Dissolving Tablet Technologies," Pharm. Tech. 27:92-100 (2003).

Price, T.M, et al., "Single-Dose Pharmacokinetics of Sublingual Versus Oral Administration of Micronized 17β-Estradiol," Obstet, Gynecol. 89:340-345 (1997).

Rawas-Qalaji, M. et al., "Fast-Disintegrating Sublingual Epinephrine Tablets: Effect of Drug and Tablet Dimensions on Tablet Characteristics," AAPS 7(52):Abstract W5220 (2005).

Rawas-Qalaji, M. et al., "Sublingual epinephrine tablets versus intramuscular injection of epinephrine: Dose equivalence for potential treatment of anaphylaxis," J. Allergy Clin. Immunol. 117(2):398-403 (Feb. 2006).

Rawas-Qalaji, M. et al., "Fast-Disintegrating Sublingual Epinephrine Tablets: Effect of Epinhophrinc Load on Tablet Characteristics," AAPS PharmSciTech 7(2) Article 41: E1-E7 (2006).

Rawas-Qalaji, M. et al., "Fast-Disintegrating Sublingual Epinephrine Tablets: Long Term Stability Study," AAPS 7(52) Abstract W5219 (2005).

Rawas-Qalaji, M. et al., "Formulation of Fast-Disintegrating Sublingual Epinephrine Tablets for the First-Aid Treatment of Anaphylaxis Away From Health Care Facilities," AAPS 6(4) Abstract W4178 (2004).

Rawas-Qalaji, M. et al., "Evaluation of the Effect of Changing Tablet Dimensions on the Characteristics of Fast-disintegrating Sublingual Epinephrine Tablets for the First-Aid Treatment of Anaphylaxis Away From Health Care Facilites," AAPS 6(4) Abstract 4179 (2004).

Rawas-Qalaji, M. et al., "Epinephrine for the Treatment of Anaphylaxis: Do All 40mg Sublingual Epinephrine Tablet Formulations with Similar In Vitro Characteristics Have the Same Biaavailability? "Biopharm, Drug Dispos. 27:427-435 (2006).

Sastry, S. et al., *Drug Del. To the Oral Cavity: Molecule to Market*, Chapter 13, pp. 331-316 (2005), eds. Taylor & Francis, CRC Press.

Sastry, S. et al., "Recent technological advances in oral drug delivery—a review," Pharm Sci. Technol. Today 3:138-145 (2000).

Scavone, J.M. et al., "The pharmacokinetics and pharmacodynamics of sublingual and oral alprazolam in the post-prandial state," Bur. J. Clin. Pharmacol. 42:439-443 (1992).

Schiermbier, S. and Schmidt, P., "Fast dispersable ibuprofen tablets,"Eur. J. Pharm. Sci, 15;295-305 (2002).

Sharma, N. et al., "Manufacturing Technology Choices for Mouth Dissolving Tablets," Pharma. Tech. North America 10-15 (2003).

Simons, F. Estelle, "First-aid treatment of anaphylaxis to food: Focus on epinephrine," J. Allergy Clin, Immunol. 113:837-844 (2004).

Simons, K.J. et al., "Sublingual epinephrine administration in humans: A preliminary study," J. Allergy Clin. Immunol. 113 (Suppl. 1):S260 (2004).

Simons, F. Estelle, "EpiPen Jr versus EpiPen in young children weighing 15 to 30 kg at risk for anaphylaxis," 3. Allergy Clin. Immunol. 109(1):171-175 (2002).

Simons, F. Estelle et al., "Outdated EpiPen and EpiPen Jr. autoinjectors: Past their Prime?" J. Allergy Clin. Immunol. 105:1025-1030 (2000).

Spenard, J. et al., "Placebo-Controlled Comparative Study of the Anxiolytic Activity and of the Pharmacokinetics of Oral and Sublingual Lorazepam in Generalized Anxiety," Biopharm. Drug Dispos. 9:457-464 (1988).

Sugimoto; M. et al., "The Preparation of Rapidly Disintegrating Tablets in the Mouth," Pharm. Dev. Technol, 6:487-493 (2001).

Verma, R. and Garg, S., "Current Status of Drug Delivery Technologies and Future Directions," Pharma. Technol. On-Line 25:1-4 (2001).

Watenabe, Y. et al, "New Compressed Tablet Rapidly Disintegrating in Saliva in the Mouth Using Crystalline Cellulose and a Disintegrant," Biol. Pharm. Bull. 18:1308-1310 (1995).

S.F. Kemp et al.; Epinephrine: the drug of choice for anaphylaxis. A statement of the world Allergy Organization; Wiley Online Library—https://onlinelibrary.wiley.com—Allergy European Journal of Allergy and Clinical Immunology; copyright 1999 retrieved Apr. 29, 2018.

K. Simons et al.; Epinephrine and its use in anaphylaxis: current issues; Current Opinion in Allergy and Clinical Immunology; copyright 2010 ; 10:254-361.

J. Soar et al.; Emergency treatment of anaphylactic reactions—guidelines for healthcare providers resuscitation, May 2008; 77(2): 157-69; https://www.ncbi.nlm.nih.gov/pubmed/18358585; retrieved Apr. 29, 2018.

M. Rawas-Qaiaji et al.; Sublingual epinephrine tablets versus intramuscular injection of epinephrine: Dose equivalence for potential treatment of anaphylaxis; vol. 117, No. 2, pp. 398-403; Journal of Allergy and Clinical Immunology Feb. 2006.

M. Rawas-Qaiaji et al.; Epinephrine for the treatment of anaphylaxis: Do all 40 mg Sublingual epinephrine tablet formulations with similar In Vitro Characteristics Have the same Bioavailability? Biopharmaceutic & Drug Disposition; 27; 427-425; Online Wiley InterScience; www.interscience.wiley.com; copyright 2006.

P. Saxena et al. ; Sublingual versus vaginal route of misoprostol for cervical ripening prior to surgical termination of first trimester abortions; Eur J. Obtet Gynocol. Reprod Bio.; https://www.ncbi.

(56) References Cited

OTHER PUBLICATIONS nlm.nih.gov/pubmed/ 16139942; copyright Mar. 1, 2006; 125(1): 109-13—retrieved Apr. 24, 2012.
R. Ousama et al.; An Electronic Tongue: Evaluation of the Masking Efficacy of Sweetening and/or Flavoring Agents on the Bitter Taste of Epinephrine; AAPS PhamSciTech, vol. 11, No. 2, Jun. 2010.
M. Rawas-Qaiaji et al.; Fast-disintegrating Sublingual tablets : Effect of epinephrine load on tablet characteristics; AAPS PhamSciTech; Apr. 28, 2006, 7 (2) article 41—https://www.aapspharmscitech.org.
International Search Report and Written Opinion dated Aug. 20, 2014 for PCT/US14/31579.
Final Office Action for U.S. Appl. No. 15/882,399 dated Sep. 27, 2018.
Response filed Sep. 19, 2018 with European Patent Office for EP patent application No. 14 768 584.6.
U.S. Appl. No. 15/288,745: Restriction requirement dated Jul. 5, 2017; Response dated Sep. 5, 2017 Office Action dated Sep. 20, 2017; Response dated Jan. 22, 2018 Notice of Allowance and Interview Summary dated Feb. 27, 2018; Response and IDS dated May 29, 2018 (142 pages).
U.S. Appl. No. 15/288,745: Office Action dated Jun. 8, 2018; IDS dated Jun. 11, 2018; Response and IDS dated Sep. 10, 2018; IDS submitted Sep. 28, 2018 and Oct. 2, 2018; Notice of Allowance and interview summary dated Oct. 18, 2018 (85 pages).
For EP Application 14 768 584.6 (regional stage of PCT/US2014/31579): claim amendments dated May 12, 2016; second examiners report dated May 28, 2018 (10 pages).
For EP Application 14 768 584.6 (regional stage of PCT/US2014/31579): European Search Report dated Aug. 10, 2016 (8 pages).
Final Office Action for U.S. Appl. No. 15/262,961 dated Jul. 24, 2018.
Response for U.S. Appl. No. 15/262,961 filed Oct. 9, 2018.
For Canadian Patent Application No. 2,853,084: Office Action dated Oct. 25, 2018 (3 pages).
For U.S. Appl. No. 15/882,399: Office Action dated Mar. 22, 2018; Response dated Jun. 22, 2018 (24 pages).
Final Office Action for U.S. Appl. No. 15/882,399 dated Sep. 27, 2019.
RCE Response for U.S. Appl. No. 15/882,399 filed Jan. 28, 2019.
Final Office Action dated Apr. 30 2019, for U.S. Appl. No. 15/358,743 45 pages.
Response filed May 2, 2019, to Office Action from European Patent Office or EP Patent Application No. 14 768 584.6, 11 pages.
Examination Report for Canadian Patent Application No. 2,876,883, 4 pages; dated May 22, 2019.
European Search Report for EP Patent Application No. 12 842 206.0, dated Jul. 1, 2019.
Ting Qiao et al., Conjugation of Catecholamines on Magnetic nanoparticles coated with Sulfonated Chitosan; Science Direct, vol. 380, Issue 1-3, pp. 169-174; May 5, 2011.
Response filed Apr. 24, 2019 for Canadian Patent Application No. 2,853,084.
Response to Office Action for U.S. Appl. No. 15/882,399 filed Jul. 26, 2019.
Office Action for U.S. Appl. No. 15/882,399 dated Mar. 29, 2019.
Office Action for EP Patent Application No. 14 768 584.6, dated Sep. 26, 2019.
Office Action for U.S. Appl. No. 16/225,609 dated Oct. 8, 2019.
Merriam Webster Definition of "Microcrystal" dated Sep. 26, 2019.
Collins Dictionary Definition of "Microparticle" retrieved Sep. 26, 2019.
Office Action for U.S. Appl. No. 16/377,810, dated Oct. 9, 2019.
Office Action for Canadian Patent Application No. 2,853,084: dated Sep. 12, 2019.
European Search Report for EP Patent Application No. 13812628.9 dated Jul. 25, 2019.

* cited by examiner

METHODS FOR FABRICATION OF EPINEPHRINE BITARTRATE NANOPARTICLES AND EPINEPHRINE BITARTRATE NANOPARTICLES FABRICATED THEREBY

CROSS REFERENCE TO RELATED APPLICATIONS

This application is a continuation of U.S. application Ser. No. 13/582,346, filed Aug. 31, 2012; which is a National Stage of International Application No. PCT/US2011/026604, filed Mar. 1, 2011; which claims the benefit of the priority of U.S. Provisional Patent Application No. 61/309,136, filed Mar. 1, 2010; the content of each of which is hereby incorporated by reference in its entirety.

FIELD OF THE INVENTION

The invention generally relates to compositions and methods for treatment of conditions responsive to epinephrine (also known as adrenaline), particularly to compositions and methods for emergency treatment of conditions responsive to epinephrine, and most particularly to compositions including epinephrine nanoparticles for sublingual administration in treatment of conditions responsive to epinephrine.

BACKGROUND

Tablets that disintegrate or dissolve rapidly in the patient's mouth without the use of water are convenient for the elderly, young children, patients with swallowing difficulties, and in situations where water is not available. For these specially designed formulations, the small volume of saliva that is available is sufficient to disintegrate or dissolve a tablet in the oral cavity. The drug released from these tablets can be absorbed partially or entirely into the systemic circulation from the buccal mucosa or sublingual cavity, or can be swallowed as a solution to be absorbed from the gastrointestinal tract.

The sublingual route usually produces a faster onset of action than traditional orally administered tablets and the portion absorbed through the sublingual blood vessels bypasses the hepatic first pass metabolic processes (Birudaraj et al., 2004, *J Pharm Sci* 94; Motwani et al., 1991, *Clin Pharmacokinet* 21: 83-94; Ishikawa et al., 2001, *Chem Pharm Bull* 49: 230-232; Price et al., 1997, *Obstet Gynecol* 89: 340-345; Kroboth et al., 1995, *J Clin Psychopharmacol* 15: 259-262; Cunningham et al., 1994, *J Clin Anesth* 6: 430-433; Scavone et al., 1992, *Eur J Clin Pharmacol* 42: 439-443; Spenard et al., 1988, *Biopharm Drug Dispos* 9: 457-464).

Likewise, due to high buccal vascularity, buccally-delivered drugs can gain direct access to the systemic circulation and are not subject to first-pass hepatic metabolism. In addition, therapeutic agents administered via the buccal route are not exposed to the acidic environment of the gastrointestinal tract (Mitra et al., 2002, *Encyclopedia of Pharm. Tech.*, 2081-2095). Further, the buccal mucosa has low enzymatic activity relative to the nasal and rectal routes. Thus, the potential for drug inactivation due to biochemical degradation is less rapid and extensive than other administration routes (de Varies et al., 1991, *Crit. Rev. Ther. Drug Carr. Syst.* 8: 271-303).

The buccal mucosa is also highly accessible, which allows for the use of tablets which are painless, easily administered, easily removed, and easily targeted. Because the oral cavity consists of a pair of buccal mucosa, tablets, such as fast disintegrating tablets, can be applied at various sites either on the same mucosa or, alternatively, on the left or right buccal mucosa (Mitra et al., 2002, Encyclopedia of Pharm. Tech., 2081-2095). In addition, the buccal route could be useful for drug administration to unconscious patients, patients undergoing an anaphylactic attack, or patients who sense the onset of an anaphylactic attack.

Epinephrine (EP) is the drug of choice for the treatment of anaphylaxis worldwide (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844). It is available only as an injectable dosage form in ampoules or in autoinjectors. In aqueous solutions, epinephrine is unstable in the presence of light, oxygen, heat, and neutral or alkaline pH values (Connors et al., 1986, in *Chemical Stability of Pharmaceuticals: A Handbook for Pharmacists*, Wiley-Interscience Publication: New York). Feasibility studies in humans and animals have shown that EP can be absorbed sublingually (Gu et al., 2002, *Biopharm Drug Dispos* 23: 213-216; Simons et al., 2004, *J Allergy Clin Immunol* 113: 425-438). The recommended dose of EP for the treatment of anaphylaxis is about 0.01 mg/Kg: usually about 0.2 mL to about 0.5 mL of a 1:1000 dilution of EP in a suitable carrier. Based on historical and anecdotal evidence, an approximately 0.3 mg dose of EP, by subcutaneous (SC) or intramuscular (IM) injection into the deltoid muscle, has been agreed upon as the dose required for the emergency treatment of anaphylaxis. Recent studies have demonstrated that if the approximately 0.3 mg dose is administered IM into the laterus vascularis (thigh) muscle, EP plasma concentrations are higher and occur more quickly than SC or IM administration into the deltoid muscle. (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844)).

As stated above, epinephrine (EP) is typically administered either subcutaneously or intramuscularly by injection. Thus, EP injections are the accepted first aid means of delivering EP and are administered either manually or by automatic injectors. It is recommended that persons at risk of anaphylaxis, and persons responsible for children at risk for anaphylaxis, maintain one or more automatic EP injectors in a convenient place at all times.

Given the difficulties associated with manual subcutaneous or intramuscular administration of EP, such as patient apprehension related to injections or the burden of an at risk person having to always maintain an EP injector close at hand, there exists a need in the art for more convenient dosage forms which can provide immediate administration of EP, particularly to a person undergoing anaphylaxis wherein the need for injection or EP injectors is obviated.

Recently, a novel fast-disintegrating tablet suitable for sublingual (SL) administration was developed. See related U.S. applications: U.S. Provisional Patent Application No. 60/715,180; U.S. Provisional Patent Application No. 60/759,039; U.S. Utility patent application Ser. No. 11/672,503; and U.S. Utility patent application Ser. No. 11/530,360. Sublingual administration of 40 mg epinephrine as the bitartrate salt using these novel tablets resulted in a rate and an extent of epinephrine absorption similar to that achieved following intramuscular injections of 0.3 mg epinephrine in the thigh. SL doses ranging from 5 to 40 mg epinephrine as the bitartrate salt were studied to achieve equivalent plasma concentrations.

Without being bound by theory, it is thought that fabrication of epinephrine into nanoparticles and incorporation of the nanoparticles into a tablet formulation with pharmaceutically-acceptable carriers, penetration enhancers, and mucoadhesives will significantly increase the absorption of SL-administered epinephrine and will result in the reduction of SL epinephrine dose required.

SUMMARY OF THE INVENTION

The invention provides a composition, including epinephrine nanoparticles, capable of enhancing the sublingual bioavailability of epinephrine, particularly in the emergency treatment of anaphylaxis.

The invention additionally provides a method for fabrication of stabilized epinephrine nanoparticles and incorporation of the fabricated nanoparticles into orally-disintegrating and fast-disintegrating tablets.

The invention also provides a pharmaceutical composition including epinephrine nanoparticles and at least one of a pharmaceutically-acceptable carrier, penetration enhancers, and mucoadhesives for buccal or sublingual administration.

The invention additionally provides a method for treatment of an allergic emergency comprising the administration of a pharmaceutical composition including epinephrine nanoparticles to a patient diagnosed with or suspected of having an allergic emergency. The allergic emergency can be anaphylaxis, asthma, or bronchial asthma.

The invention also provides a method for treatment of a cardiac event comprising the administration of a pharmaceutical composition including epinephrine nanoparticles to a patient diagnosed with or suspected of having a cardiac event. The cardiac event can be cardiac arrest.

As described herein, buccal or sublingual oral disintegrating tablets (ODTs) are distinguished from conventional sublingual tablets, lozenges, or buccal tablets by the ODTs' ability to fully dissolve or disintegrate in less than about one minute in the mouth.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

Summary of In Vitro Diffusion Experiments and Results

The experiments described herein were carried out to assess the in vitro diffusion of epinephrine nanoparticles. The use of epinephrine nanoparticles instead of epinephrine salt was hypothesized to enhance the sublingual bioavailability of epinephrine from administration of a fast-disintegrating sublingual tablet formulation for the emergency treatment of anaphylaxis and/or treatment of other conditions responsive to epinephrine.

Methods: The diffusion of 80 µg epinephrine from four formulations, epinephrine base nanoparticles suspension (Epi-NP Susp) (size 200 nm), epinephrine solution (Epi-HBCD Sol); epinephrine base using hydroxypropyl-β-cyclodetrin as a solubilizing agent, epinephrine suspension (Epi-CMC Susp); epinephrine base using 0.3% carboxymethyl cellulose as a suspending agent, and epinephrine bitartrate solution (Epi Bit Sol), was studied over 8.5 hours using automated flow-through Franz cell system (n=6). Cumulative epinephrine concentrations in the donor cells were measured using HPLC-UV (High Performance Liquid Chromatography system with an ultraviolet detector). The cumulative epinephrine concentration versus time (AUC), maximum epinephrine flux ($J_{max}$), time to reach Jmax ($Jt_{max}$), and epinephrine permeation coefficient (Kp) for each formulation were calculated and statistically analysed using one-way ANOV and Tukey-Kramer tests, NCSS program, at a level of significance p<0.05.

Figure 1:
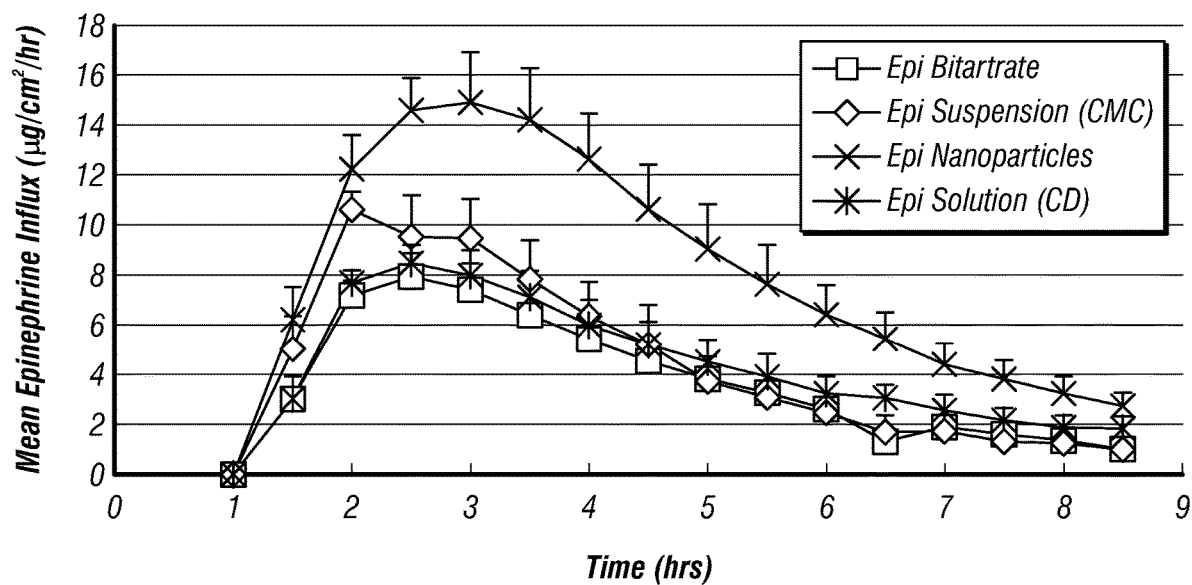
FIG. 1 is a graph showing mean epinephrine influx ($\mu g/cm^2/hr$) obtained from the tested formulations; epinephrine nanoparticles suspension (EP-NP Susp) (size 200 nm), epinephrine solution (Epi-HBCD Sol), epinephrine suspension (Epi-CMC Susp), and epinephrine bitartrate solution (Epi Bit Sol).

Results: The AUC and Jmax obtained from epinephrine nanoparticles (Epi-NP Susp), 10.4±1.7 µg/ml/hr and 15.1±1.9 µg/cm²/hr respectively, were significantly higher than epinephrine suspension (Epi-CMC Susp), 5.1±1.1 µg/ml/hr and 10.4±1.6 µµg/cm²/hr, epinephrine solution (Epi-HBCD Sol), 5.5±0.5 µµg/ml/hr and 8.6±0.3 µg/cm²/hr, and epinephrine bitartrate (Epi Bit Sol), 4.6±0.9 µg/ml/hr and 7.9±1.0 µg/cm²/hr. $Jt_{max}$ was not significantly different between the four formulations. The Kp of epinephrine nanoparticles, 0.19±0.07 cm/hr was significantly higher than epinephrine suspension, 0.13±0.002 cm/hr, epinephrine solution, 0.11±0.04 cm/hr, and epinephrine bitartrate, 0.10±0.04 cm/hr. These results are illustrated in the graph of FIG. 1.

Conclusions: In these experiments, the permeation of epinephrine nanoparticles (Epi-NP Susp) was almost 2 folds higher than the epinephrine bitartrate (Epi Bit Sol) and epinephrine solution (Epi-HBCD Sol). Epinephrine nanoparticles may have the potential to enhance the sublingual bioavailability of epinephrine compared to epinephrine salt in sublingual tablet formulation. Ex vivo and in vivo studies are contemplated and will be pursued to confirm these results.

Details of Fabrication Experiments and Results
Fabrication of Nanoparticles

Nanoparticles were fabricated from epinephrine base and epinephrine bitartrate (Bit) using high energy fluidization (microfluidization) techniques. These techniques involve the use of oversaturated solutions of various solvents, particularly water and isopropanol, at various temperatures and pressures ranging from about 8,000 psi to 30,000 psi and to about 8.3° to 43.3° C. under various passes. Particle size was measured before and after size reduction using a Mastersizer (Malvern) and/or a NiComp 370 Submicron Particle Sizer (NiComp) and nano-sized particles were confirmed using laser diffraction techniques. The particles were lyophilized (freeze-dried) using a bench top lyophilizer (ART Inc.).

Solubility Studies

In order to determine suitable vehicles to suspend epinephrine base and epinephrine bitartrate (Bit) for nanoparticle fabrication, solubility studies were carried out.

TABLE 1

Solubility

| Sample Name | Amount Dissolved % |
| --- | --- |
| Epinephrine Base solubility in water | 2.67 |
| Epinephrine Bit solubility in methanol | 10.45 |
| Epinephrine Bit solubility in isopropyl alcohol | 0.62 |
| Epinephrine Bit solubility in acetonitrile | 0.77 |
| Epinephrine Bit solubility in acetone | 1.56 |
| Epinephrine Bit solubility in hexane | 0.03 |
| Epinephrine Bit solubility in choloroform | 0.09 |
| Epinephrine Bit solubility in dichloromethane (DCM) | 0.00 |
| Epinephrine Bit solubility in tetrahydrofuran (THF) | 7.76 |
| Epinephrine Bit solubility in ethyl acetate | 0.63 |

Fabrication of nanoparticles was first attempted using epinephrine base.

Fabrication: Epinephrine Base

TABLE 2

Epinephrine Base

| Sample | Solvent | Concentration (mg/ml) | Pressure (psi) (#passes) | Particle Size Distribution (nm) (NiComp) | Sample Temperature (° C.) | Sample Color after Processing |
| --- | --- | --- | --- | --- | --- | --- |
| 1 | water | 0.3 | 30,000 | 273.9 | 43.3 | brown |
| 2 | water | 0.308 | 29,000 (1) | 334 | 18.3 | brown |
| 3 | 0.1% phosphoric acid | 1.03 | 15,000 (2) | 335 | 36.8 first pass 41.1 second pass | brown |
| 4 | 1M acetic Acid | 1.55 | 8,500 (1) 15,000 (1) | 392 | 36.6 first pass 38.4 second pass | brown |
| 5 | water | 4.03 | 15,000 | 905.9 | 10 | brown |
| 6 | 0.1 mM sodium metabisulfite in water | 4.02 | 15,000 | 903.1 | 8.3 | brown |
| 7 | 0.1 mM sodium metabisulfite in 0.1M perchloric acid | 12.02 | 15,000 | 903.1 Note: 111.5 nm (80)% and 2.2 nm (20%) using Zetasizer machine | 8.3 | pink |
| 8 | water | 10.0 | 8,000 (1) 15,000 (1) | 447 | | |

Nanoparticles of epinephrine base in various sizes were produced ranging in diameter from about 273.9 to 905.9 nm.

First Sample

The sample consisted of 30 mg epinephrine in 100 ml of distilled water. One pass at 30,000 psi was applied and a temperature of 43.3° C. was measured after the process. The sample was processed using a M-110P High Energy Fluidizer™ (Microfluidics). The particles were lyophilized using bench top lyophilizer (ART Inc.). The mean particle size obtained was 273.9 nm using the NiComp 370 Submicron Particle Size Analyzer. The sample was stored in the refrigerator.

Second Sample

This sample consisted of 30 mg epinephrine in 100 ml of distilled water. One pass at 29,000 psi was applied and a temperature of 18.3° C. was measured after the process. The homogenizer was setup using the cooling coil. Ice packs and tap water were used to cool the pressurized sample to 14° C. The mean particle size obtained was 334.3 nm using the NiComp 370 Submicron Particle Size Analyzer. The sample was stored in the refrigerator.

Third Sample

This sample was prepared in 0.1% phosphoric acid. The phosphoric acid solution was prepared by diluting 0.5 ml of phosphoric acid 85% (Mallinckrodt Chemicals, LOT H39A04, Exp. Sep. 30, 2011) in 500 ml of distilled water. The epinephrine sample was prepared by weighing 103 mg of epinephrine base into 100 ml of 0.1% phosphoric acid solution prior to sample passes. Two passes at 15,000 psi were applied to the sample. In the first pass a temperature of 36.8° C. was measured after the process and in the second pass a temperature of 41.1° C. was obtained. The mean particle size obtained was 334.6 nm using the NiComp 370 Submicron Particle Size Analyzer. The sample was stored in the refrigerator.

Fourth Sample

This sample was prepared in 1M acetic acid. The 1M acetic acid solution was prepared by diluting 27.5 ml of glacial acetic acid (BDH Aristar, ACS, USP, FCC grade, LOT 200929924) in 500 ml of distilled water. The epinephrine sample was prepared by weighing 155 mg of epinephrine base into 100 ml of 1M acetic acid solution. The M-110p was flushed with distilled water, followed by acetic acid solution prior to sample passes. Two passes were applied to the sample, in the first pass a pressure of 8,500 psi was applied and a temperature of 36.6° C. was measured in the collected sample. In the second pass a pressure of 15,000 psi was applied and a temperature of 38.4° C. was measured in the collected sample. The mean particle size obtained was 392.0 nm using the NiComp 370 Submicron Particle Size Analyzer. The sample was stored in the refrigerator.

Fifth, Sixth, and Seventh Samples

These samples were prepared in a dark room to avoid light. The homogenizer was setup using the cooling coil. Ice packs and tap water were used to cool the pressurized samples. Higher drug concentration was used in the seventh sample since the acidic solvent tends to dissolve more drug than the other previously-used solvents.

Visual Observations

The main problem was discoloration (a brown color formed) due to degradation. All samples were discolored to a pinkish color and then became dark brownish after processing, indicating epinephrine instability. The seventh sample (water+0.1 mM sodium metabisulfite+0.1 M perchloric acid) discolored to a slightly pinkish color. 0.1 mM sodium metabisulfite+0.1 M perchloric acid usually provided optimum stability for epinephrine for several months.

Figure 2A:
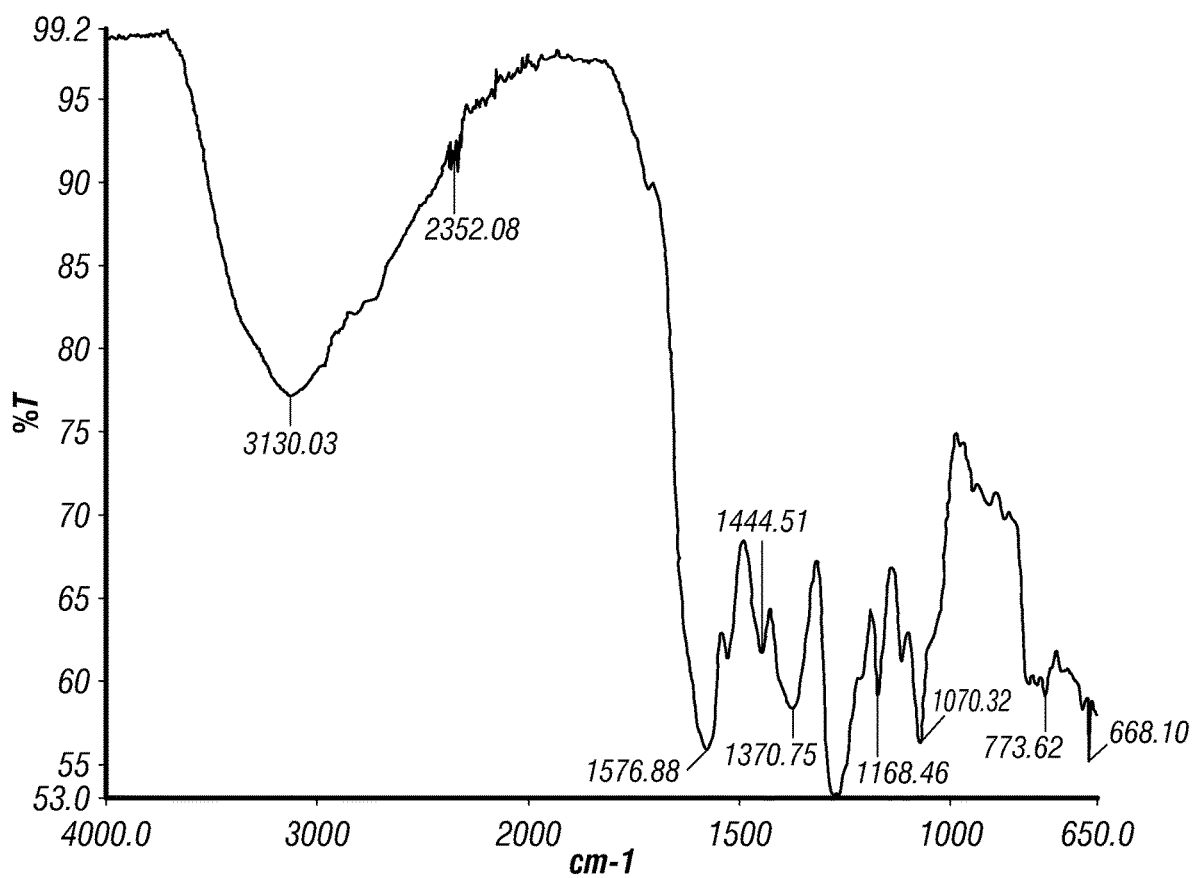
FIG. 2A is a Fourier Transform Infrared (FT-IR) spectrum for epinephrine base nanoparticles after fabrication (processing).
Figure 2B:
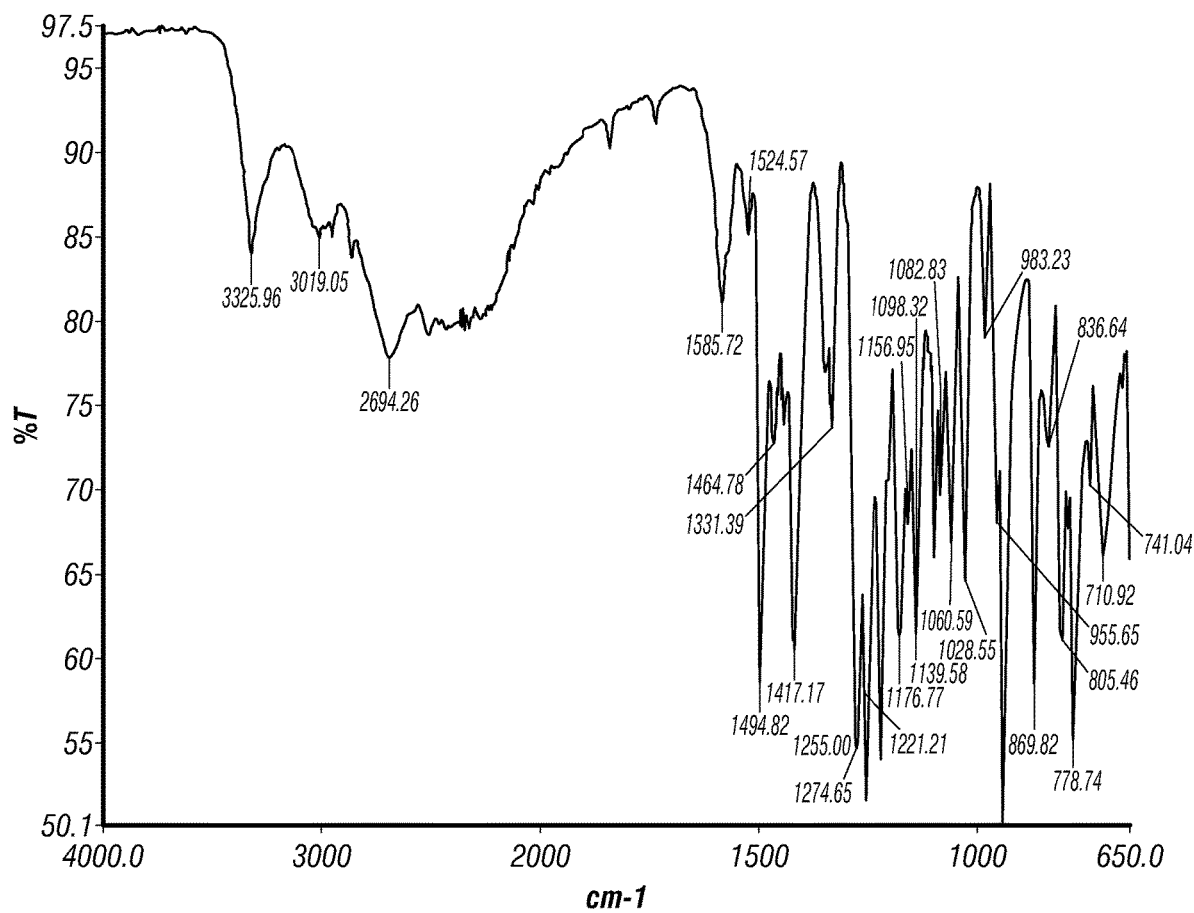
FIG. 2B is a FT-IR spectrum for epinephrine base nanoparticles before processing.

The FT-IR spectrum for epinephrine base before (FIG. 2B) is different from the FT-IR spectrum after processing (FIG. 2A), which reflects the degradation that occurs during processing. The epinephrine base required stabilization with acetic acid or phosphoric acid (in the suspension media) and cooling of the reaction chamber to minimize degradation.

Sizing

The first sample (epinephrine in water) was used.

TABLE 3

Sizes of Epinephrine Base Before and After Processing

| Sample | Before Fabrication (nm) | After Fabrication (110 F., 30 Kpsi) (nm) |
|---|---|---|
| 1 | 33030 | 273.9 |
| 2 | 32530 | |
| 3 | 33160 | |
| Mean | 32900 | |
| Standard Error | 192.04 | |
| Standard Deviation | 332.62 | 179 |

Figure 3:
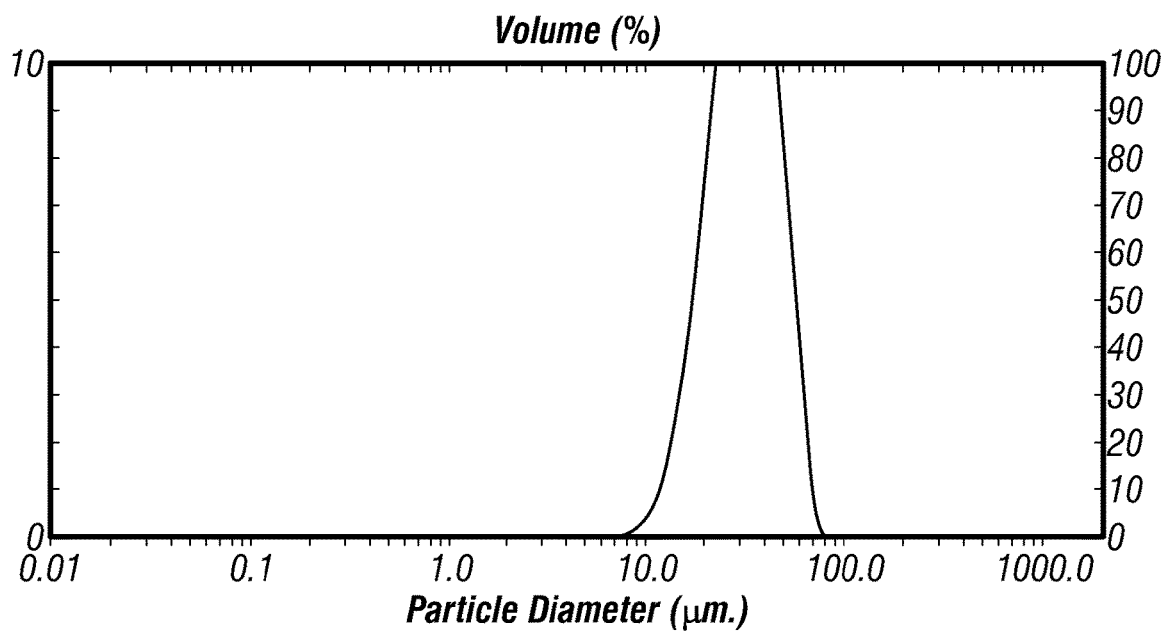
FIG. 3 illustrates particle size distribution of epinephrine base measured before size reduction (processing) using Mastersizer.
Figure 4:
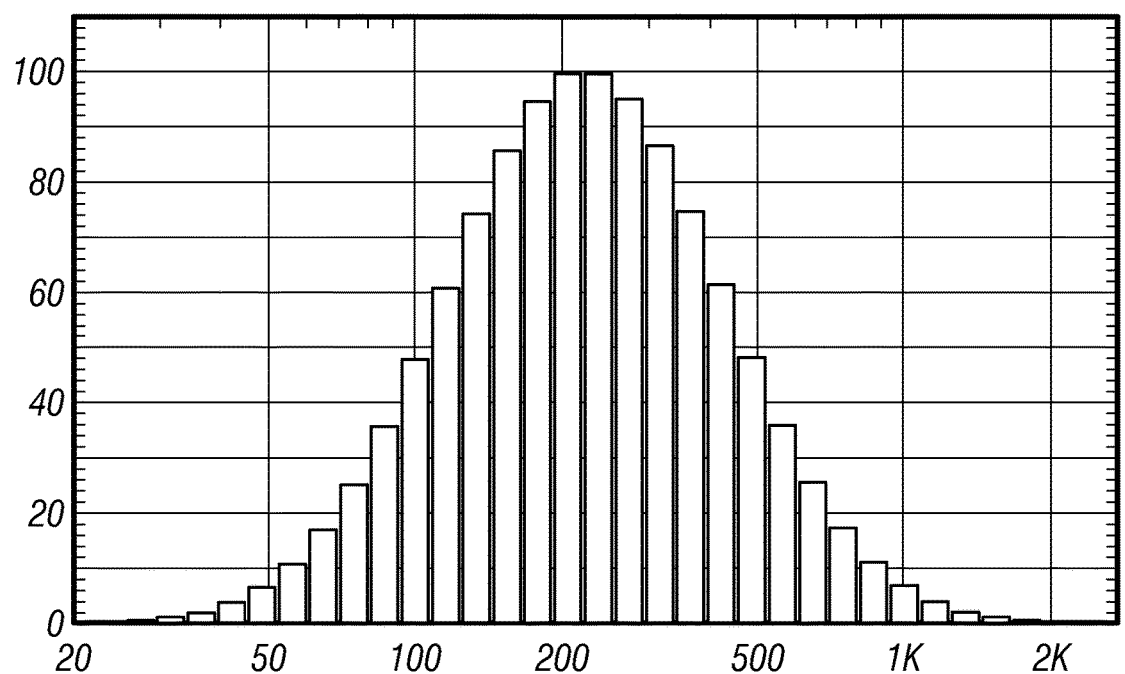
FIG. 4 illustrates particle size distribution of epinephrine base measured after size reduction using NiComp 370.

The epinephrine particle size reduction to nanosize was successful. The mean±SD size was reduced from 32.91±0.33 μm (FIG. 3) to 273.9±179.0 nm (FIG. 4).

Fabrication: Epinephrine Bitartrate (Bit)

In light of the instability associated with the epinephrine base particles, fabrication using the epinephrine salt, epinephrine bitartrate, was pursued.

Isopropyl alcohol (IPO) was selected as a suspending vehicle based on its safety profile and the solubility study previously performed (see above) for several solvents.

TABLE 4

Epinephrine Bitartrate (Bit)

| Sample | Solvent | Concentration (mg/ml) | Pressure (psi) (# passes) | PSD nm (NiComp) |
|---|---|---|---|---|
| 1 | IPO | 7.0 | 15,000 (1) | 43,000 |
| 2 | IPO | 3.5 | 25,000 (1) | 8,766 |
| | | | 25,000 (1) | 3,879 |
| 3 | IPO | 0.875 | 25,000 (1) | 3,971 |
| 4 | IPO | 0.70 | 25,000 (6) | 2,368 |
| | | | 25,000 (16) | 1,203 |

Observations

Nanoparticles of epinephrine bitartrate in various sizes were produced ranging in diameter from about 43,000 to 1,203 nm.

The first sample, a suspension of 7.0 mg/ml, was used as a stock suspension and was used to prepare the other dilutions. Thus, the passes are additive and each (pass) represents an additional pass to the previous dilution.

After ten passes in the last run, includes samples one, two, three, and the first pass of sample 4, the particle size distribution (PSD) did not change (no effect after ten passes) according to NiComp readings.

The fourth sample was processed six times (6 passes in one step) followed by an additional ten passes (for a total of sixteen passes continuously).

The epinephrine bitartrate (salt form of epinephrine) was more stable than the epinephrine base, did not show any discoloration, and tolerated the fabrication conditions (nanomilling).

First Sample

Figure 5:
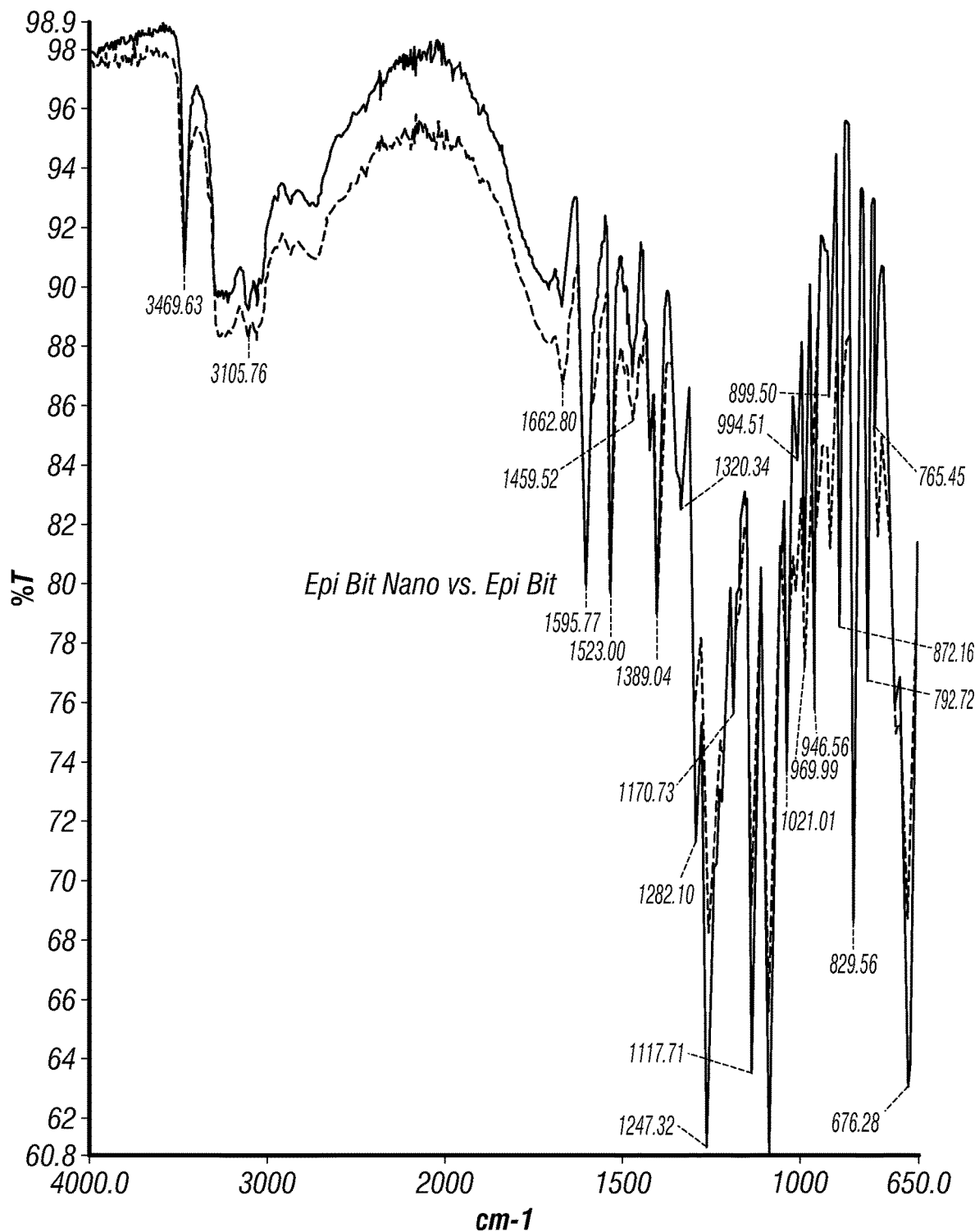
FIG. 5 is a FT-IR spectrum for epinephrine bitartrate nanoparticles before and after processing (nanoparticle fabrication).

The particle size distribution (PSD) of epinephrine bitartrate after processing (fabrication) using Zetasizer was 5000 nm (60%) and 500-1000 nm (30-40%). The yield of fabricated epinephrine bitartrate after drying was 68%. The Fourier Transformation Infrared (FT-IR) spectrums are similar in both epinephrine bitartrate before and after processing (FIG. 5).

Details of In Vitro Diffusion Experiments and Results

Epinephrine diffusion was evaluated using an automated, flow through cell system (n=6) under the following parameters:

Flow rate: 50 μl/minute

Donor cell orifice area: 0.2 cm$^2$

Sample volume added to donor cell: 200 μl

Medium in receptor cells: phosphate buffer (pH=5.8)

Membrane: 7 Spectra/Por® dialysis membranes (1000 MWt cutoff).

Epinephrine, base or salt equivalent to 400 μg/ml epinephrine base, in the following four different formulations were used:

1) Epinephrine base nanoparticles suspension (Epi-NP Susp).

2) Epinephrine base suspension using 0.3% carboxymethyl cellulose as a suspending agent (Epi-CMC Susp).

3) Epinephrine base solution using hydroxypropyl-β-cyclodetrin as a solubilizing agent (Epi-HBD Sol).

4) Epinephrine bitartrate solution (Epi Bit Sol).

200 μl from each of the four formulations was spiked into the donor cells. Samples were collected every 30 minutes for 8.5 hours and analyzed by High Performance Liquid Chromatography (HPLC) for epinephrine concentration.

HPLC Analysis

HPLC analysis was performed under the following parameters:

PerkinElmer HPLC system with ultraviolet (UV) detector
Column: Econspher (Alltech), $C_{18}$ 4.6×150 mm, 3 μm
Mobile Phase: USP 26$^{th}$ Edition, 2003
Flow Rate: 1 ml/minute
Detection Wavelength: 280 nm
Retention Time: epinephrine 4.8 minutes Statistical Analysis of Results Results were statistically analyzed using one-way ANOV and Tukey-Kramer tests, NCSS program, at a level of significance p<0.05.

Mean±SD values of cumulative epinephrine concentration versus time (AUC), maximum epinephrine flux (JMax), time to reach JMax (t/Max), and epinephrine permeation coefficient (Kp) for each formulation was calculated.

Results

Figure 6A:
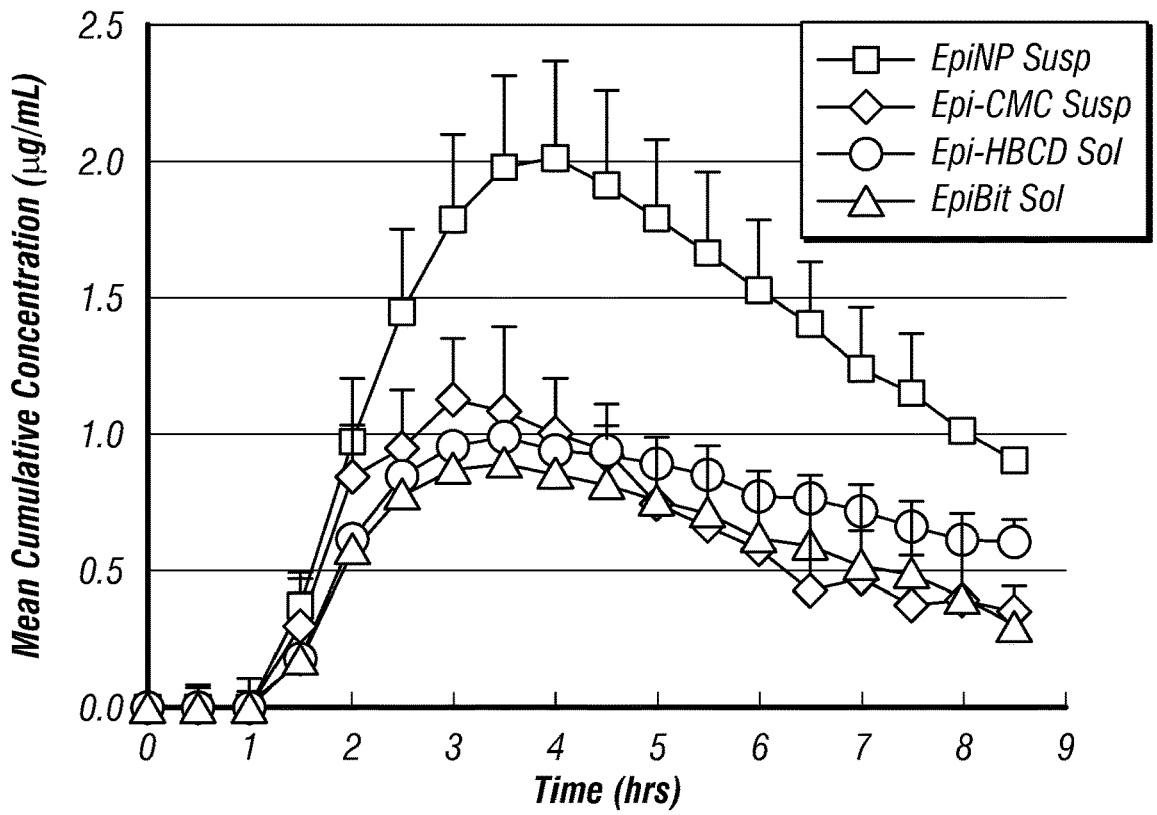
FIG. 6A is a graph showing the AUC (mean cumulative epinephrine concentration) ($\mu g/ml$) obtained from the four tested formulations; EP-NP Susp, Epi-CMC Susp, Epi-HBCD Sol, and Epi Bit Sol.
Figure 6B:
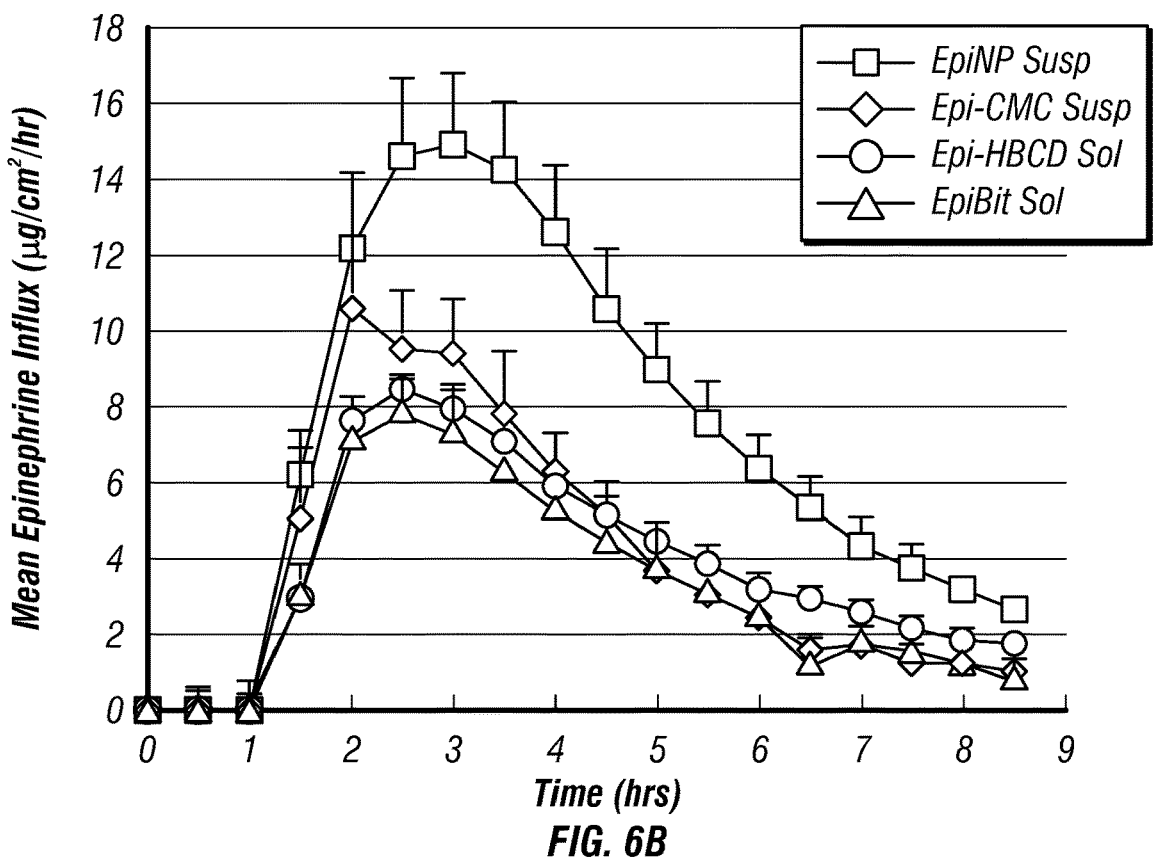
FIG. 6B is a graph showing mean epinephrine influx ($\mu g/cm^2/hr$) obtained from the tested formulations; EP-NP Susp, Epi-CMC Susp, Epi-HBCD Sol, and Epi Bit Sol.

Mean±SD values of cumulative epinephrine concentration versus time (AUC), maximum epinephrine flux (JMax), and epinephrine permeation coefficient (Kp) obtained from EP-NP Susp were significantly higher than Epi-CMC Susp, Epi-HBCD Sol, and Epi Bit Sol (p<0.05). The time to reach JMax (tfMax) was not significantly different between the four formulations. These results are illustrated in the graphs of FIGS. 6A-B.

TABLE 5

In Vitro Diffusion Data

| | Formulation: | | | |
|---|---|---|---|---|
| | Epi-NP Susp | Epi-CMC Susp | Epi-HBCD Sol | Epi Bit Sol |
| AUC (μg/ml/hr) | 10.4 ± 1.7* | 5.1 ± 1.1 | 5.5 ± 0.5 | 4.6 ± 0.9 |
| JMax (μg/cm²/hr) | 15.1 ± 1.9* | 10.4 ± 1.6 | 8.6 ± 0.3 | 7.9 ± 1.0 |
| $t_{Jmax}$ (hr) | 9.41 ± 0.26 | 9.41 ± 0.50 | 10.17 ± 0.10 | 10.12 ± 0.09 |
| Kp (cm/hr) | 0.19 ± 0.07* | 0.13 ± 0.002 | 0.11 ± 0.04 | 0.10 ± 0.04 |

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, epinephrine nanoparticles, pharmaceutical tablets, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A method for fabricating stabilized epinephrine bitartrate nanoparticles, the method comprising:
    a) forming a mixture consisting of a pre-determined amount of epinephrine bitartrate and isopropyl alcohol, the pre-determined amount of epinephrine bitartrate combined with the isopropyl alcohol in a reaction chamber; and
    b) exposing the mixture formed in step a) to at least a first pass at a pre-determined pressure and a pre-determined temperature, thereby fabricating the stabilized epinephrine bitartrate nanoparticles.

2. The method according to claim 1, wherein, in the forming step, the pre-determined amount of epinephrine bitartrate has a concentration between about 0.70 mg/ml and about 7.0 mg/ml in the isopropyl alcohol.

3. The method according to claim 1, wherein the pre-determined pressure for the exposing step is selected in a range from about 8,000 psi to about 30,000 psi and the pre-determined temperature for the exposing step is selected in a range from about 8.3 to about 43.3° C.

4. The method according to claim 1, further comprising exposing the mixture formed in step a) to multiple passes subsequent to the first pass, the multiple passes at a same or a different pre-determined pressure and at a same or a different pre-determined temperature from that of the first pass.

5. The method according to claim 1, further comprising lyophilizing the stabilized epinephrine bitartrate nanoparticles fabricated by carrying out steps a)-b).

6. The method according to claim 1, further comprising measuring particle size of the stabilized epinephrine bitartrate nanoparticles after fabrication, the particle size less than a 1000 nm.

* * * * *